(12) United States Patent  
Badri et al.

(10) Patent No.: US 10,094,795 B2
(45) Date of Patent: Oct. 9, 2018

(54) HIGH RESOLUTION RESISTIVITY MEASUREMENTS ON CORE PLUGS

(71) Applicant: SCHLUMBERGER TECHNOLOGY CORPORATION, Sugar Land, TX (US)

(72) Inventors: Mohammed Badri, Al-Khobar (SA); Mohammed Fadhel Al-Hamad, Eastern Province (SA); Abdullah Habelreeh, Dhahran (SA); Wael Abdallah, Dhahran (SA); Reza Taherian, Missouri City, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 85 days.

(21) Appl. No.: 14/990,689

(22) Filed: Jan. 7, 2016

(65) Prior Publication Data

US 2017/0199141 A1 Jul. 13, 2017

(51) Int. Cl.
*G01R 31/02* (2006.01)
*G01N 27/02* (2006.01)
*G01N 27/04* (2006.01)

(52) U.S. Cl.
CPC ......... *G01N 27/028* (2013.01); *G01N 27/041* (2013.01)

(58) Field of Classification Search
USPC ................................. 324/691–712
See application file for complete search history.

(56) References Cited

U.S. PATENT DOCUMENTS

| 4,907,448 A | 3/1990 | Givens |
| 7,132,831 B2 * | 11/2006 | Brabers ................ G01V 3/02 324/357 |
| 7,459,920 B2 * | 12/2008 | Mizukami ............ G01N 27/048 324/444 |
| 2002/0060576 A1 | 5/2002 | Tominaga |
| 2010/0163433 A1 | 7/2010 | Horn |
| 2014/0218037 A1 | 8/2014 | Slater et al. |

FOREIGN PATENT DOCUMENTS

CN 101149406 A 3/2008

OTHER PUBLICATIONS

Search Report and Written Opinion of International Application No. PCT/US2016/063437 dated Mar. 3, 2017, 13 pages.

* cited by examiner

*Primary Examiner* — Vincent Q Nguyen

(57) ABSTRACT

A tool having two current electrodes, three or more voltage electrodes, and a measurement device capable of making electrical measurements is provided, along with a sample. With electrical connectivity to the sample, one current electrode is disposed at one location on the sample while the other current electrode is disposed at another location on the sample, and the three or more voltage electrodes are disposed on the sample intermediate the two current electrodes. An electric current is passed through the sample. The measurement device is used to make a first set of electrical measurements that involve a first pair of voltage electrodes and to make a second set of electrical measurements that involve a second pair of voltage electrodes. The first set of electrical measurements is compared to the second set of electrical measurements. It is inferred whether the sample has heterogeneous electrical properties using the compared electrical measurements.

20 Claims, 7 Drawing Sheets

HIGH RESOLUTION RESISTIVITY MEASUREMENTS ON CORE PLUGS

BACKGROUND

Resistivity of core plugs is routinely measured in the laboratory. The standard method of performing this measurement is the so-called "four-electrode measurement" in which electrical current is injected along the axis of the cylindrical core plug and the voltage drop along the length is measured. FIG. 1 shows a schematic drawing of this technique. The core plug (sample) 110 is sandwiched between two current electrodes 120a and 120b causing current to flow axially along the cylinder. Two ring or point (voltage) electrodes 140a and 140b, separated by 1 inch (2.54 cm), are used to measure the voltage drop along the length of the sample. As drawn, the voltage electrodes are rings of conductive wire wrapped around the circumference of the core plug 110. An LCR meter 160 (i.e., inductance L, capacitance C, resistance R measurement device) provides current to the electrodes 120a and 120b and measures the voltage across electrodes 140a and 140b. The resistance of the sample is calculated using Ohm's law:

$$R = \frac{V}{I} \tag{1}$$

Given the geometry (e.g., length, cross-sectional area) of the core sample 110, the resistivity of the core material can be determined from the resistance.

The four electrode measurement is the technique of choice for most applications because it is not affected by the contact impedance between the current electrodes 120a and 120b with the rock sample 110. In a variation of the technique called the "two-electrode measurement", current electrodes 120a, 120b are also used to measure the voltage drop along the entire length of the sample. However, this method cannot account for the contact impedance inherently present between the metal electrodes 120a, 120b and solid rock end surfaces. In yet another approach called "three-electrode measurement", the sample is energized as in FIG. 1, but the voltage is measured between one of the current electrodes 120a, 120b and one of the voltage electrodes 140a, 140b.

In the four electrode measurement, the resistance determined from the measured voltages and currents is not the resistance of the entire core plug 110. Rather it is the resistance of the part of the rock located between the two voltage electrodes 140a, 140b (which is typically 1 inch (2.54 cm)). Again, the resistivity of the material can be determined using the determined resistance and the known geometric parameters of the sample. With this arrangement the depth of investigation of the measurement is sufficient to sample the entire cross-section of the core sample 110. However, the axial resolution of the measurement is approximately 1 inch (2.54 cm), which is often too coarse. That is, a rock inhomogeneity along the length and within the cross-section of core may be overlooked. Due to the heterogeneous nature of the rock, in some applications it is desirable to know the resistivity at higher axial resolution such as 0.1 in (0.254 cm) or 0.25 in (0.635 cm), for example. In addition, it is desirable to know the resistivity of the sample at such high resolutions along the entire length of the core sample.

SUMMARY

A tool having two current electrodes, three or more voltage electrodes, and a measurement device capable of making electrical measurements is provided, along with a sample. With electrical connectivity to the sample, one current electrode is disposed at one location on the sample while the other current electrode is disposed at another location on the sample, and the three or more voltage electrodes are disposed on the sample intermediate the two current electrodes. An electric current is passed through the sample. The measurement device is used to make a first set of electrical measurements that involve a first pair of voltage electrodes and to make a second set of electrical measurements that involve a second pair of voltage electrodes. The first set of electrical measurements is compared to the second set of electrical measurements. It is inferred whether the sample has heterogeneous electrical properties using the compared electrical measurements.

This summary is provided to introduce a selection of concepts that are further described below in the detailed description. This summary is not intended to identify key or essential features of the claimed subject matter, nor is it intended to be used as an aid in limiting the scope of the claimed subject matter.

BRIEF DESCRIPTION OF THE DRAWINGS

The present disclosure is understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. Embodiments are described with reference to the following figures. The same numbers are generally used throughout the figures to reference like features and components.

DETAILED DESCRIPTION

Figure 1:
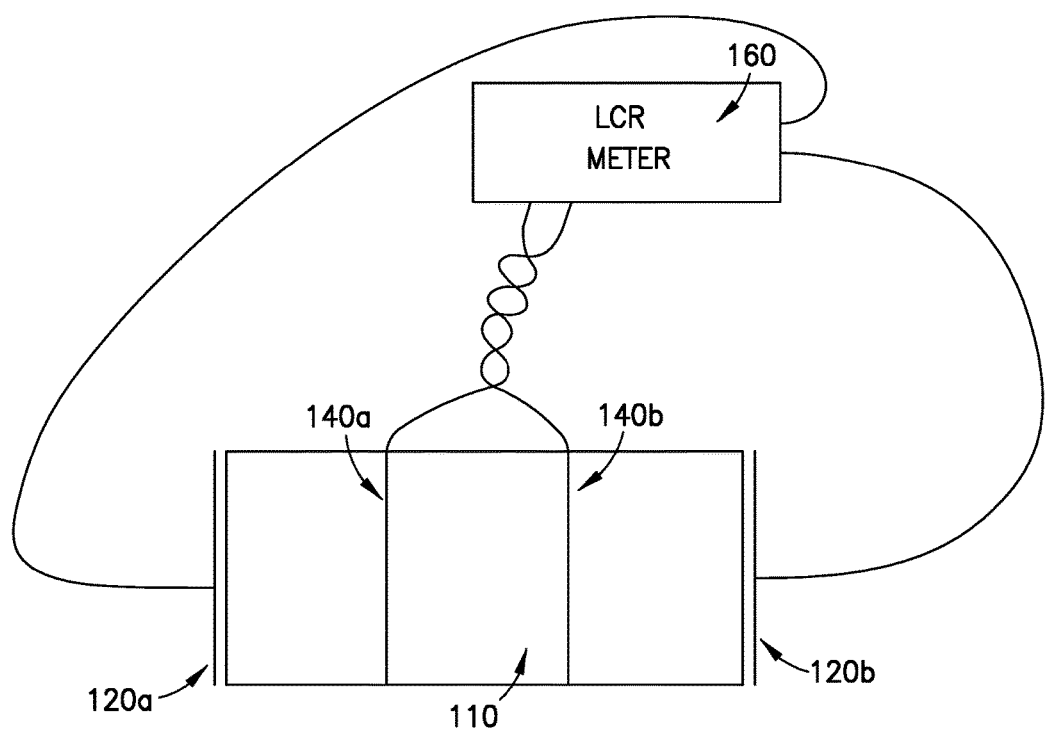
FIG. 1 is a schematic drawing of a prior art four electrode measurement system.

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact.

Some embodiments will now be described with reference to the figures. Like elements in the various figures may be referenced with like numbers for consistency. In the following description, numerous details are set forth to provide an understanding of various embodiments and/or features. However, it will be understood by those skilled in the art that some embodiments may be practiced without many of these details and that numerous variations or modifications from the described embodiments are possible. As used here, the terms "above" and "below", "up" and "down", "upper" and "lower", "upwardly" and "downwardly", and other like terms indicating relative positions above or below a given point or element are used in this description to more clearly describe certain embodiments. However, when applied to equipment and methods for use in wells that are deviated or horizontal, such terms may refer to a left to right, right to left, or diagonal relationship, as appropriate. It will also be understood that, although the terms first, second, etc. may be used herein to describe various elements, these elements should not be limited by these terms. These terms are only used to distinguish one element from another.

The terminology used in the description herein is for the purpose of describing particular embodiments only and is not intended to be limiting. As used in the description and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

A system and method to determine the resistivity, at high resolution, along the length of a core sample is disclosed. The number of voltage electrodes used may be increased (relative to existing tools) and arranged so as to be closer to each other (i.e., decreased voltage electrode spacing). Such arrangements lead to more resistivity measurements along the length of the core sample. Different combinations of voltage electrodes can be used to make resistance measurements with varying depths of investigation and axial resolution. Thus, different combinations of these measurements can be used to obtain axial resistivities with high resolution and deep depths of investigation. Some combinations allow relatively small resistivity anomalies buried within the body of the core sample to be detected.

Figure 2:
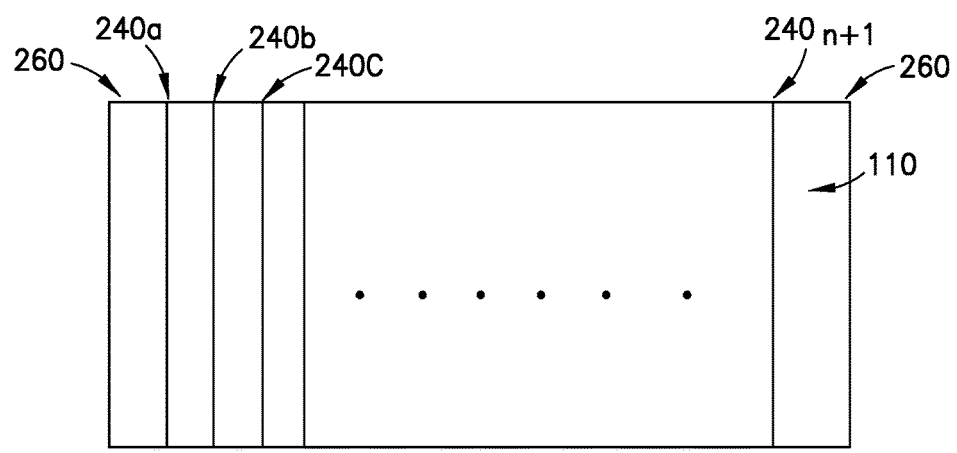
FIG. 2 is a schematic drawing of a measurement system having a plurality of voltage electrodes, in accordance with the present disclosure.

In the embodiment of FIG. 2, n+1 voltage electrodes are wrapped around the circumference of the core plug at some desired, small offset distance from each other. FIG. 2 shows the core plug 110 with the wrapped voltage electrodes 240a, 240b, $240_{(n+1)}$. Note there will be a slight dead zone 260 at the each end of the core plug 110. If the voltage electrodes are evenly spaced, the distance between any two adjacent electrodes is L/n, where L is the physical length of the core plug 110 minus the length of the two dead zones 260. A typical core length is 50 mm and, disposing nine electrodes on the sample, for example, and assuming dead zones of 1 mm on each side, the distance between any pair of adjacent voltage electrodes is 48/8 or 6 mm, which is a measure of the axial resolution of the resistivity measurement.

Figure 3:
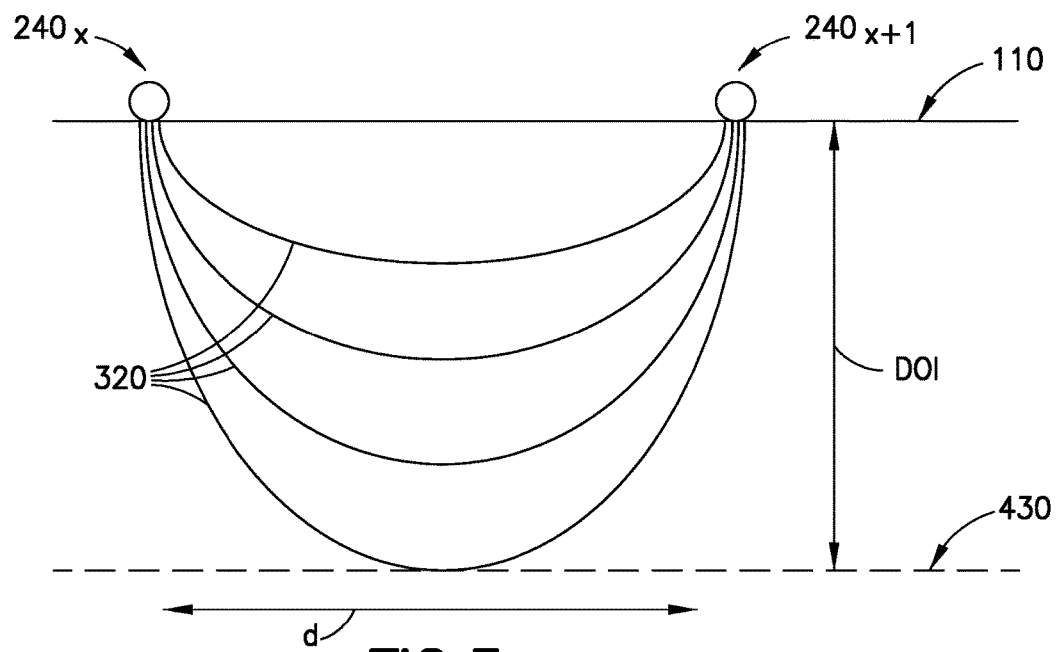
FIG. 3 is a schematic drawing showing how the depth of investigation (DOI) of the measurement is reduced as the voltage electrodes get closer to each other, in accordance with the present disclosure.
Figure 4:
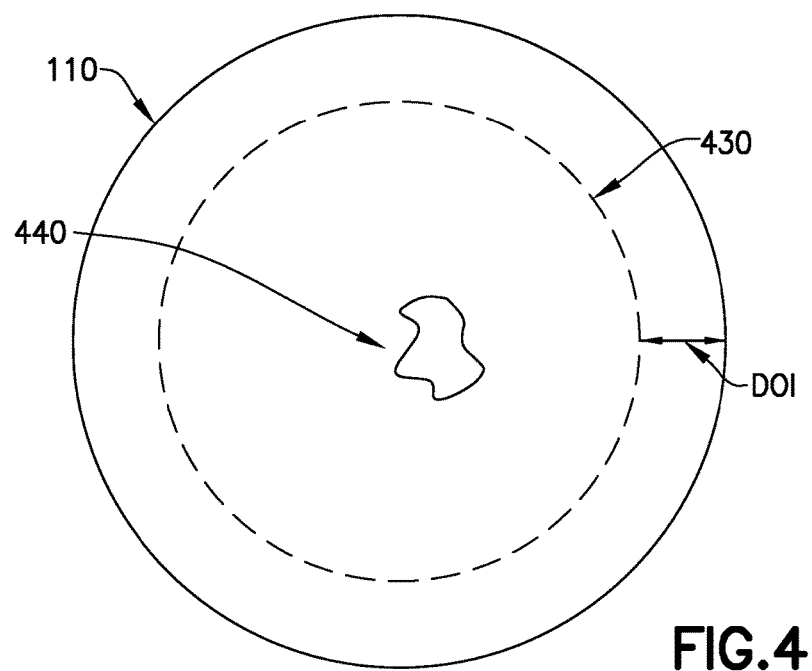
FIG. 4 is a schematic drawing of an electrical anomaly embedded in the interior of a core plug, in accordance with the present disclosure.

As the voltage electrodes get closer to each other, the depth of investigation (DOI) of the measurement suffers. This is demonstrated in FIG. 3 where a small portion of the core plug 110 with two voltage electrodes $240_x$ and $240_{(x+1)}$ are shown. The two voltage electrodes are separated by a distance d and, as the electric field lines 320 demonstrate, the maximum penetration depth of the electric field radially into the core plug 110 is approximately the same as d. Thus, in the example embodiment above, the voltage measurements by electrodes that are 6 mm apart will be sensitive to about 6 mm into the core plug 110. Since core plugs are typically 38 mm (1.5 inch) in diameter, the measurement will be insensitive to any resistivity anomaly that is deeper than 6 mm from the surface of the core plug 110. This issue is better illustrated in FIG. 4. Core plug 110 is shown in an end view cross-section with an anomaly 440 close to the center of the plug 110. Since the DOI extends only to the circle 430 and is not as large as the radius of the core plug, the measurement will not be sensitive to the anomaly 440. This serves to demonstrate that one cannot increase the resolution and the DOI of measurements at the same time, at least not by simply reducing the offset distance between measurement electrodes.

Figure 5:
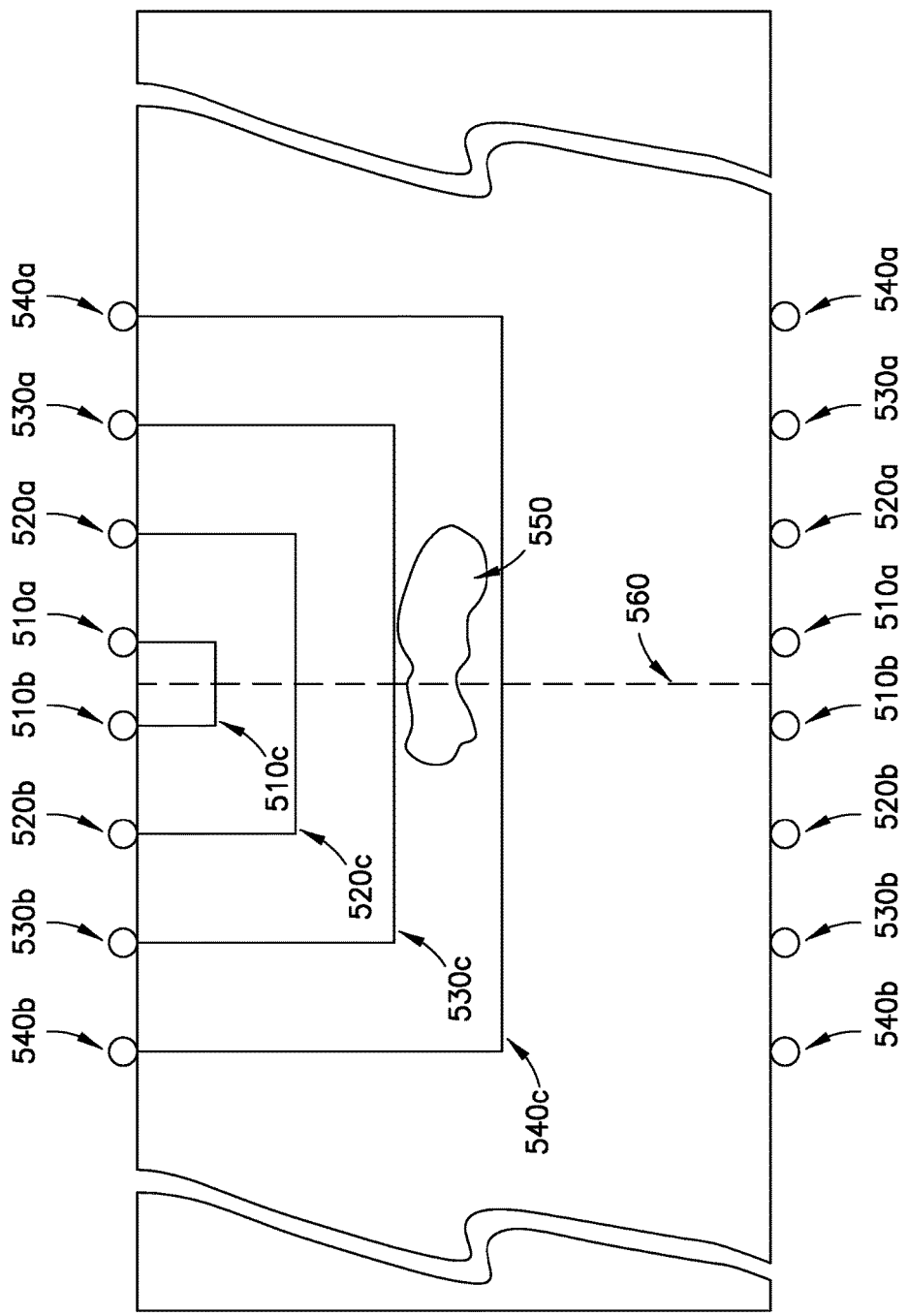
FIG. 5 is a cross-sectional view of core plug along the axis of cylindrical plug with voltage electrode pairs wrapped around the perimeter of the core, in accordance with the present disclosure.

That said, measurements between electrodes at different offset distances provide measurements at different DOIs that can detect an otherwise undetected anomaly inside the core plug 110. FIG. 5 shows a cross-sectional view of core plug 110 along the axis of cylindrical plug. The voltage measuring electrode pair's 510a-510b, 520a-520b, 530a-530b, and 540a-540b are wrapped around the perimeter of the core and are also shown in cross-sectional view. Voltage measurements are made between each electrode pair. As was discussed and illustrated in FIG. 3, the DOI of measurements from each of these measurement pairs is roughly proportional to the distance between the two electrodes comprising the pair. For convenience of illustration, a symbolic rectangular field line (i.e., a "block") 510c is drawn to demonstrate the approximate DOI of measurements from the 510 electrode pair. Similar blocks are drawn for the remaining electrode measurement pairs, demonstrating the DOI and the corresponding electrode measurement pair spacing increases progressively for measurements from the 510 to 540 electrode pairs. There are similar blocks originating from the lower (with respect to FIG. 5) portions of the electrode pairs 510 to 540, but, for clarity, those are not drawn.

If a rock sample is homogeneous, or at least the resistivity does not change dramatically with respect to DOI, the four electrode pairs of this embodiment should yield approximately the same resistivity. However, if there is an inhomogeneity 550 with different resistivity present somewhere in the core, it will affect the measurements differently. The inhomogeneity 550 will only affect the measurements with DOI greater than or equal to the distance from the core face (cylindrical surface) to the inhomogeneity. In the example of FIG. 5, the inhomogeneity 550 is drawn to fall outside the DOI of the 510, 520, and 530 electrode pairs, but is within the DOI of the 540 electrode pair. For this case the resistivity determined from the first three electrode pairs will be the same, while the resistivity determined from the 540 electrode pair will be higher/(lower) if the resistivity of inhomogeneity 550 is higher/(lower) than that of the surrounding material.

Figure 6:
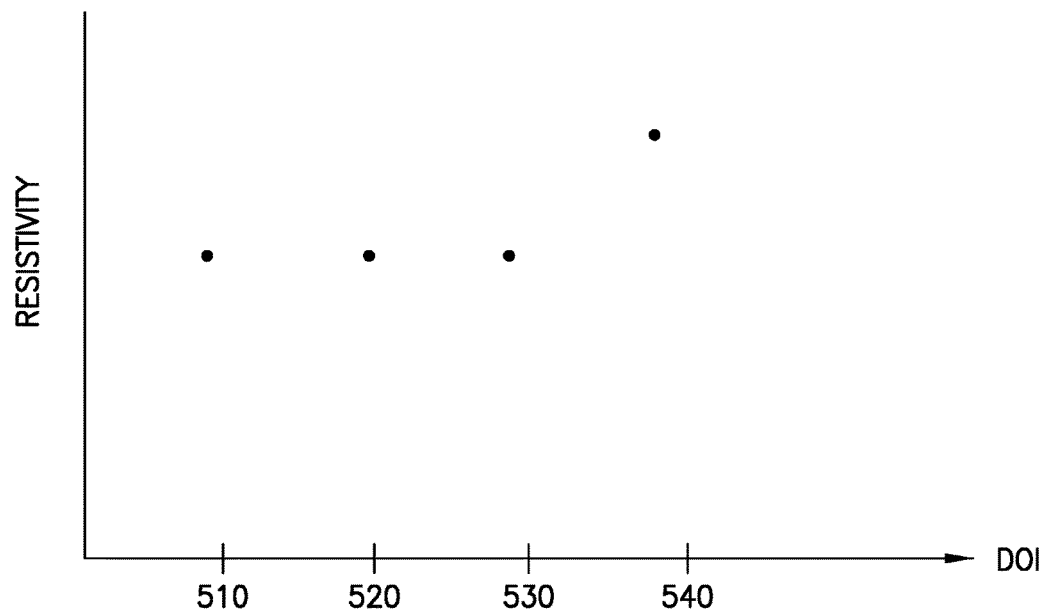
FIG. 6 is a plot of expected measurements for each measurement pair of the embodiment of FIG. 5, in accordance with the present disclosure.

The expected measurements for each measurement pair are plotted in FIG. 6 and demonstrate the possibility of comparing measurements from electrode pairs with different DOIs to learn about an unknown anomaly buried within the structure of the rock. The results of FIG. 6 can be further improved using more accurate calculations of the DOIs for the electrode pairs. With a more precise quantitative model, it is possible to more precisely calculate the resistivity of the anomaly 550.

Figure 7:
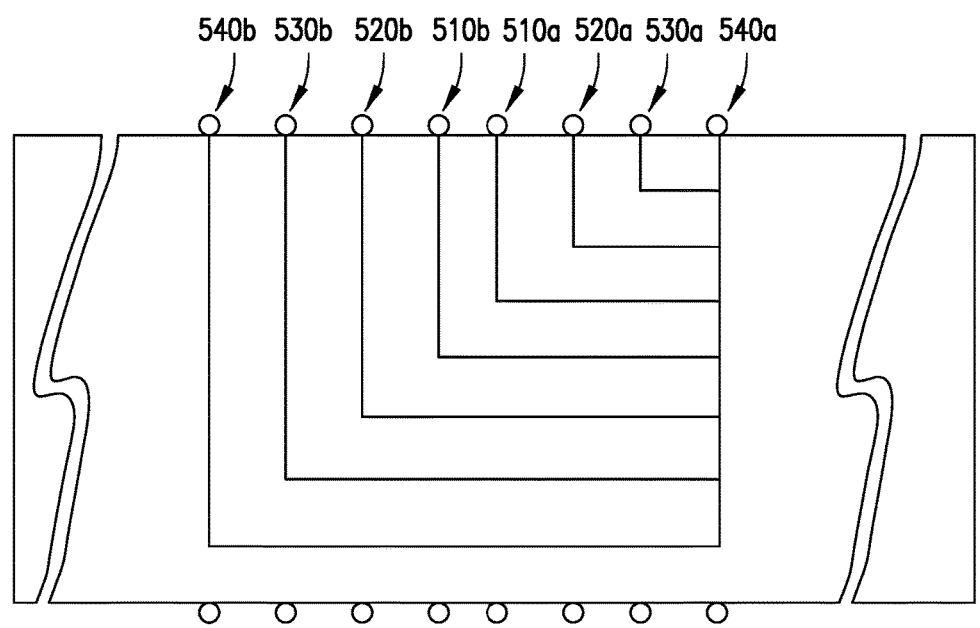
FIG. 7 is a schematic drawing of an embodiment using a distal voltage electrode as a pair member common to all voltage electrode pairs, in accordance with the present disclosure.

In the example of FIG. 5, the electrodes are used symmetrically so that the center of measurements is along the line 560. In that embodiment, the number of measurements and DOIs is 4. In other embodiments the electrodes can be combined as demonstrated in FIG. 7. Unlike the embodiment of FIG. 5, in this embodiment one of the electrodes, say 540a, is paired with every other electrode, increasing the number of measurements to 7 and also increasing the maximum DOI. The extra information obtained from this embodiment can be used to locate an anomaly with better precision and resolution. Combining the electrode pairs is not limited to these two scenarios; any other pairing of electrodes or combinations of electrode pairs can be used, leading to a wealth of measurements and corresponding information about the resistivity variation within the rock core.

The above discussion teaches how different combinations of the electrodes can be used to produce many measurements with various DOIs. In this manner detailed information about the heterogeneity of the rock is obtained. In addition, finite element models (FEMs) can use the many measurements to obtain an image of the heterogeneities that may exist in the rock. To do that, the rock is modeled as comprising many small voxels (volume elements) with initially assumed or assigned resistivities. Given the known electrode locations, expected resistivities for the various combinations of electrodes are calculated. For a particular voxel for which measurement data are available, the difference between the resistivity determined from measurements and the resistivity computed by the FEM is calculated and the resistivity value for that voxel is varied so as to minimize that difference. That is done for all such voxels. A plot of the voxels with corresponding resistivities highlights the locations of heterogeneities in the rock sample.

Figure 8:
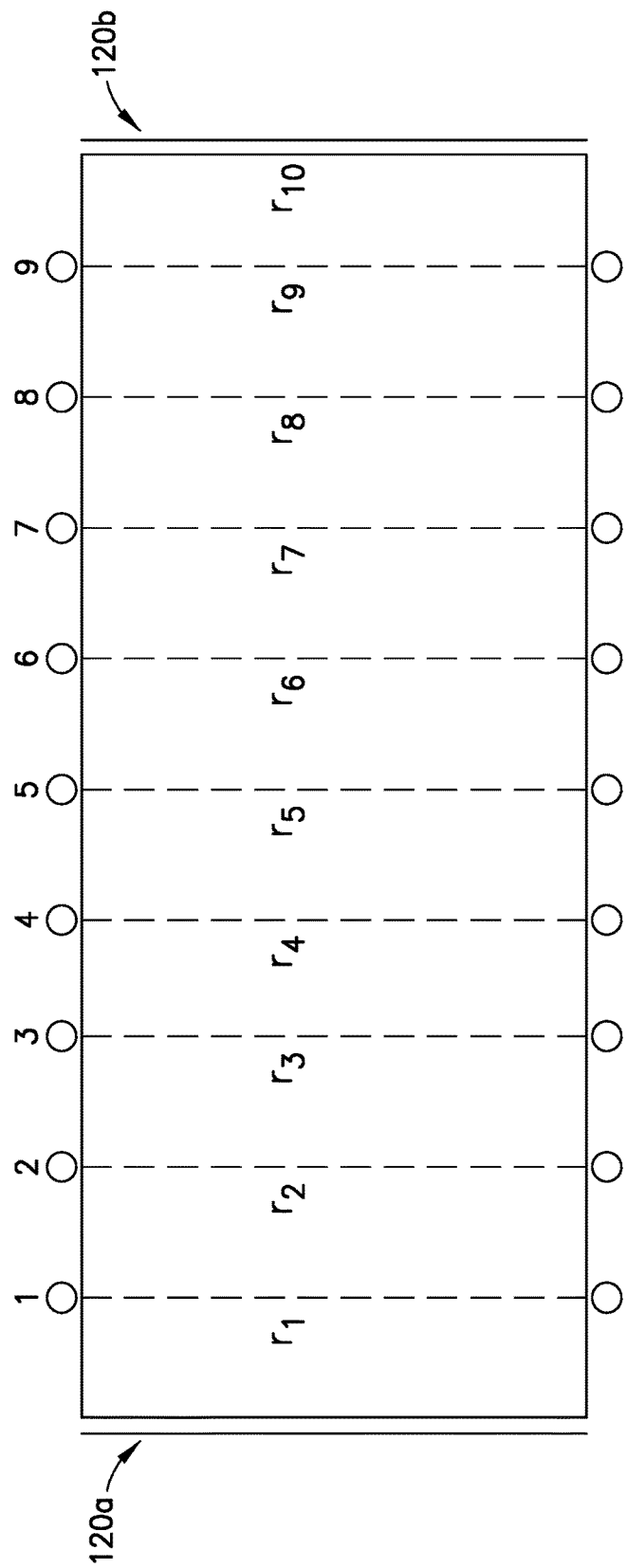
FIG. 8 is a schematic drawing of an embodiment in which a sample having current electrodes on each end has been covered along its length with nine voltage electrodes, in accordance with the present disclosure.

As was mentioned above, the standard four electrode measurement places the voltage electrodes 1 inch (2.54 cm) apart, leading to a resolution of 1 inch (2.54 cm) and the number of measurements is one. In one or more embodiments disclosed herein, the electrodes are paired in various combinations to determine the resistivity of individual thin slices along the length of the core plug. FIG. 8 shows an example wherein current electrodes 120a and 120b are present and the core has been covered along its length with nine voltage electrodes, labelled 1 through 9. Further, the slice of rock between any two adjacent electrodes is assumed to have a constant resistivity $r_i$, with i ranging from 1 to 10. Electrodes 1 and 2, for example, can be paired for a resistivity measurement, but as mentioned before, this measurement will have a rather shallow DOI and will not sample the entire slice of the rock. Assuming electrodes 1 to 9 are wound such that the distances between two adjacent electrodes are the same, it may be assumed a measurement pairing electrodes 1 and 4 has a sufficiently deep DOI to sample the entire rock cross-section, albeit at lower axial resolution. In this case the measurement $R_{14}$ measures a sum of resistivities from the three slices that lie between electrodes 1 and 4. That is (see FIG. 8):

$$R_{14}=r_2+r_3+r_4 \qquad (2)$$

Electrode 1 may also be paired with electrode 5, leading to a new measurement:

$$R_1=r_2+r_3+r_4+r_5 \qquad (3)$$

Subtracting Eq. (2) from Eq. (3) yields $r_5$ which is the resistivity of a single rock slice but at a DOI that is deep enough to cover the entire rock cross-section. This process can be continued to the end, leading to high resolution resistivities for slices 5 through 9. To determine $r_1$, $r_2$, and $r_3$, it suffices to choose a second electrode such as 7 and vary the first electrode from 1 to 4. Again, the shortest distance between electrodes is 4 to 7 which was assumed to be large enough to provide a measurement with sufficient DOI. In this case:

$$R_{47}=r_5+r_6+r_7 \qquad (4)$$

$$R_{37}=r_4+r_5+r_6+r_7 \qquad (5)$$

so the difference between Eq. (4) and Eq. (5) yields $r_4$. Repeating with electrodes 2 and 1, $r_3$ and $r_2$ are obtained.

This technique works well for measuring the resistivity of all slices except the first and last ($r_1$ and $r_{10}$ in FIG. 8). However, these two resistivities can be measured using the three-electrode approach. For the configuration shown in FIG. 8, current is injected using electrodes 120a and 120b and the voltage can be measured between 120a and a third electrode such as electrode 1, for example. In this case $r_1$ is determined. In an approach similar to what is described for the four electrode measurement (equations 2 and 3), electrode 1 can be replaced by other electrodes such as 2, 3, etc., and more accurate values for $r_1$ determined. With this approach, $r_2$, $r_3$, etc., from the three electrode approach are side products and can be compared to measurements using the two electrode approach to estimate the error, if any, that was introduced by using one of the current electrodes for the voltage measurement. Resistivity $r_{10}$ can be determined in the same manner as $r_1$ using the other current electrode 120b paired with one of the nearby voltage electrodes.

Figure 9:
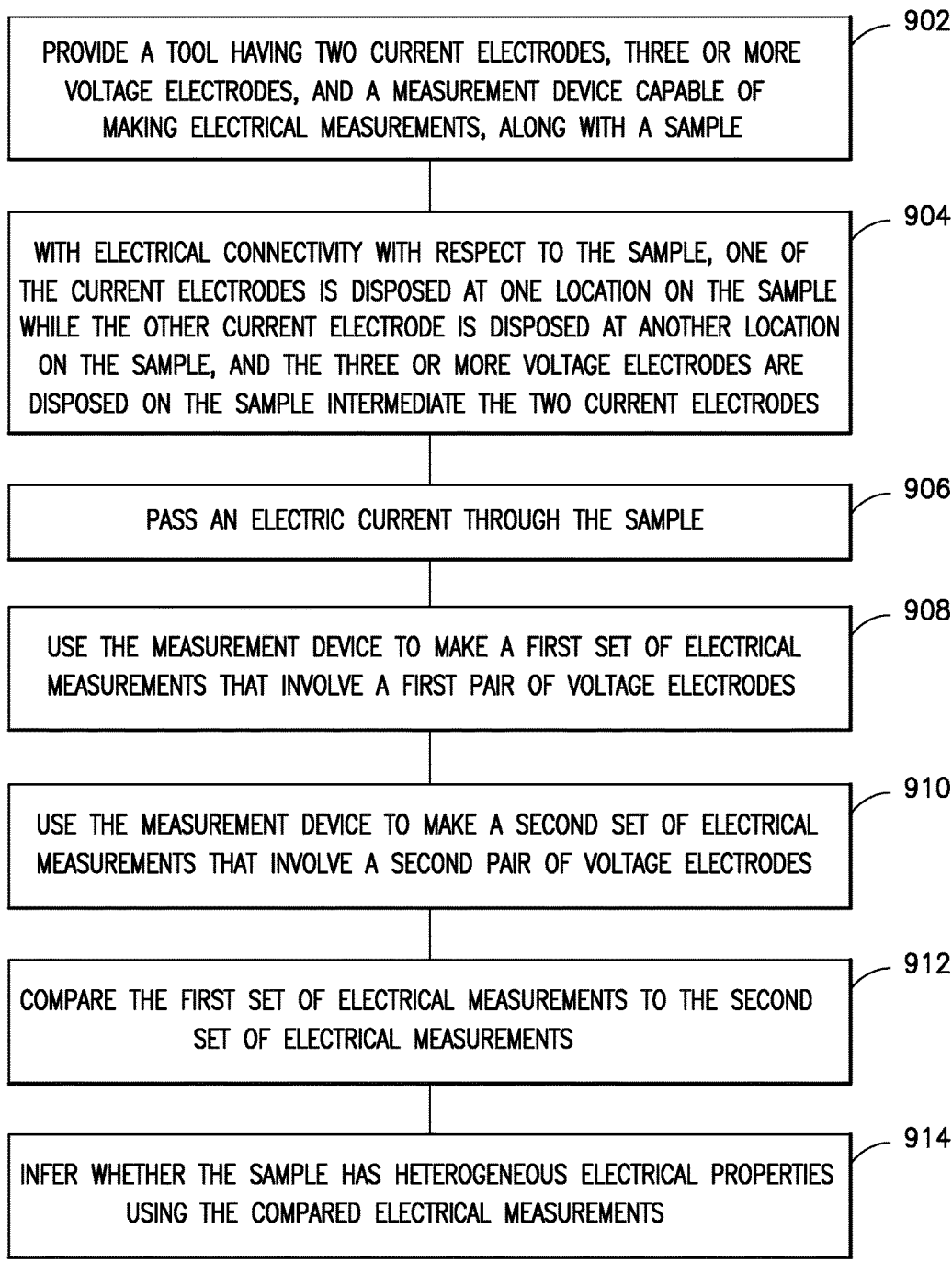
FIG. 9 is a flowchart for using a measurement system to infer whether a sample has heterogeneous electrical properties using compared electrical measurements, in accordance with the present disclosure.
Figure 10:
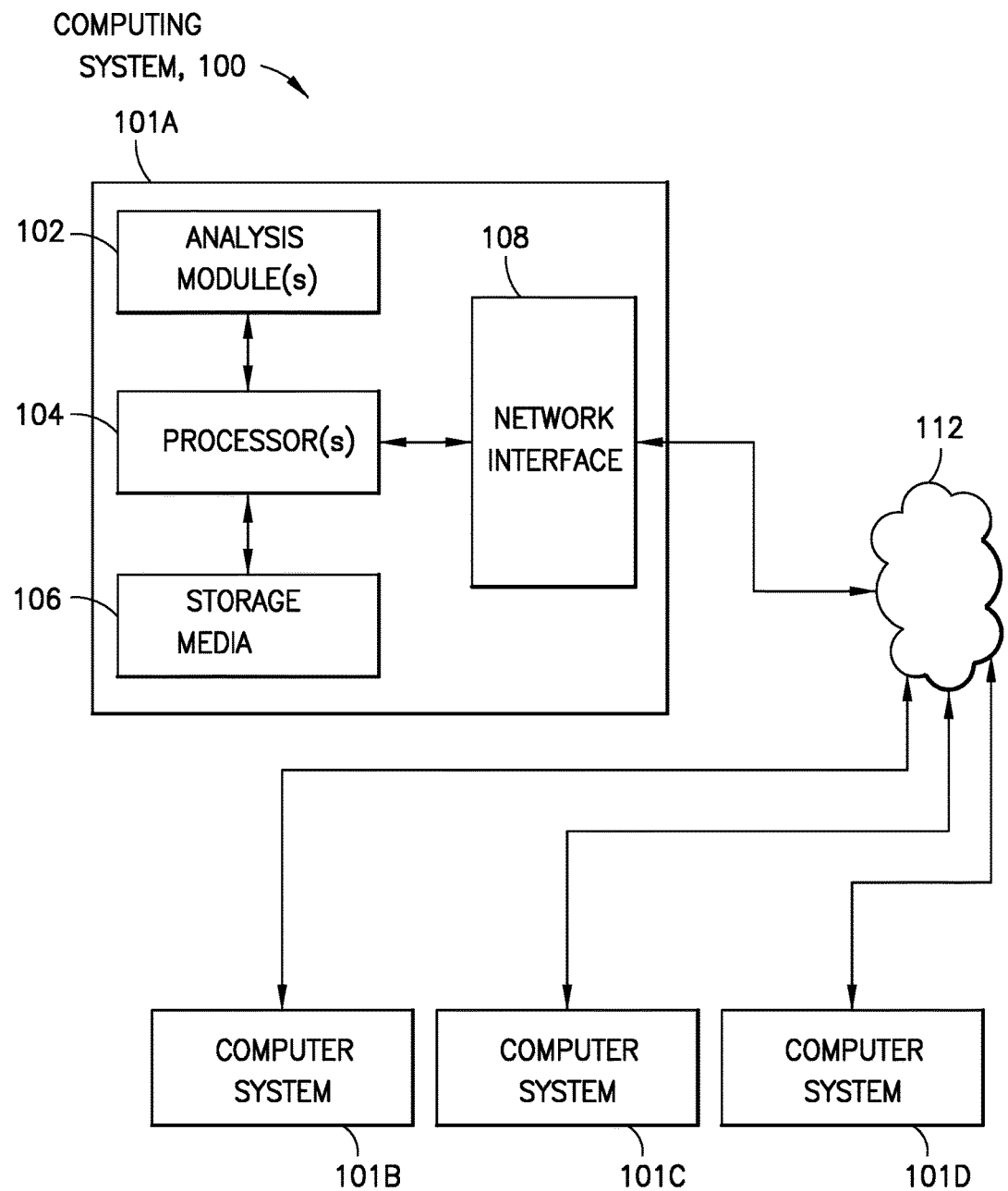
FIG. 10 is a schematic drawing of a computer system suitable for use with embodiments described herein, in accordance with the present disclosure.

FIG. 9 is a flowchart for one embodiment to infer whether a sample has heterogeneous electrical properties. A tool having two current electrodes, three or more voltage electrodes, and a measurement device capable of making electrical measurements is provided, along with a sample (902). With electrical connectivity with respect to the sample, one of the current electrodes is disposed at one location on the sample while the other current electrode is disposed at another location on the sample, and the three or more voltage electrodes are disposed on the sample intermediate the two current electrodes (904). An electric current is passed through the sample (906). The measurement device is used to make a first set of electrical measurements that involve a first pair of voltage electrodes (908) and to make a second set of electrical measurements that involve a second pair of voltage electrodes (910). The first set of electrical measurements is compared to the second set of electrical measurements (912). It is inferred whether the sample has heterogeneous electrical properties using the compared electrical measurements (914).

Embodiments of the method/process described above can be performed by a processor. The term "processor" should not be construed to limit the embodiments disclosed herein to any particular device type or system. A processor may be part of a computer system 100. That is, the computer system 100 may include a computer processor 104 (e.g., a microprocessor, microcontroller, digital signal processor, or general purpose computer) for executing any of the embodiments described above.

The computer system may further include a memory 106 such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device.

Some of the embodiments described above can be implemented as computer program logic or analysis module(s) 102 for use with the computer processor 104. The computer program logic 102 may be embodied in various forms, including a source code form or a computer executable form. Source code may include a series of computer program instructions in a variety of programming languages (e.g., an object code, an assembly language, or a high-level language such as C, C++, or JAVA). Such computer instructions can be stored in a non-transitory computer readable medium (e.g., memory) and executed by the computer processor 104. The computer instructions may be distributed in any form as a removable storage medium with accompanying printed or electronic documentation (e.g., shrink wrapped software), preloaded with a computer system (e.g., on system ROM or fixed disk), or distributed from a server or electronic bulletin board over a communication system (e.g., the Internet or World Wide Web). Computer system 100 may include a network interface 108 to link a local computer unit 101A with other computer systems such as the internet 112 or remote computer units 101B, 101C, 101D, for example.

Alternatively or additionally, the processor may include discrete electronic components coupled to a printed circuit board, integrated circuitry (e.g., Application Specific Integrated Circuits (ASIC)), and/or programmable logic devices (e.g., a Field Programmable Gate Arrays (FPGA)). Any of the embodiments described above can be implemented using such logic devices.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the scope of the present disclosure, and that they may make various changes, substitutions, and alterations herein without departing from the scope of the present disclosure.

The Abstract at the end of this disclosure is provided to comply with 37 C.F.R. § 1.72(b) to allow the reader to quickly ascertain the nature of the technical disclosure. It is submitted with the understanding that it will not be used to interpret or limit the scope or meaning of the claims.

While only certain embodiments have been set forth, alternatives and modifications will be apparent from the above description to those skilled in the art. These and other alternatives are considered equivalents and within the scope of this disclosure and the appended claims. Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

What is claimed is:

1. A method, comprising:
   providing a tool having two current electrodes, three or more voltage electrodes, and a measurement device capable of making electrical measurements;
   providing a sample;
   disposing with electrical connectivity with respect to the sample one of the current electrodes at one location on the sample, the other current electrode at another location on the sample, and the three or more voltage electrodes on the sample intermediate the two current electrodes;
   passing an electric current through the sample;
   using the measurement device to make a first set of electrical measurements that involve a first pair of voltage electrodes;
   using the measurement device to make a second set of electrical measurements that involve a second pair of voltage electrodes;
   comparing the first set of electrical measurements to the second set of electrical measurements;
   inferring that the sample has heterogeneous electrical properties using the compared electrical measurements; and
   adjusting, based on the first set and the second set of electrical measurements, a finite element model (FEM) to approximate heterogeneous electrical property values.

2. The method of claim 1, wherein the sample was obtained from a subsurface formation.

3. The method of claim 1, wherein the heterogeneous electrical properties of the sample are selected from the group consisting of: resistivity, conductivity, resistance, impedance, capacitance, and inductance.

4. The method of claim 1, wherein the three or more voltage electrodes are spaced to provide various depths of investigation into the interior of the sample and high resolution measurements of the sample.

5. The method of claim 4, wherein any two voltage electrodes comprise a measurement pair and a plurality of voltage electrode measurement pairs are used to obtain the high resolution measurements and the various depths of investigation.

6. The method of claim 1, further comprising detecting a resistivity anomaly within the interior of the sample.

7. The method of claim 1, wherein any two voltage electrodes comprise a measurement pair only if the center of measurement between those two voltage electrodes substantially lies on a line on which all other centers of measurement of all other measurement pairs substantially lie.

8. The method of claim 1, wherein any two voltage electrodes comprise a measurement pair only if the most distal voltage electrode comprises one pair member of each measurement pair.

9. The method of claim 1, further comprising:
adjusting the FEM;
comparing the FEM approximate values to corresponding heterogeneous electrical property values determined from voltage electrode measurements, and
adjusting the FEM approximate values to minimize the difference between the FEM approximate values and the values determined from voltage electrode measurements.

10. The method of claim 1, further comprising:
combining measurements from particular voltage electrode pairs to form a first combined value, combining measurements from those particular voltage electrode pairs and an adjacent voltage electrode pair to form a second combined value, and determining a difference between the first combined value and the second combined value.

11. The method of claim 1, further comprising:
making a measurement of a dead zone in the sample using a current electrode as both a current electrode and a voltage electrode.

12. A method, comprising:
providing a tool having a plurality of voltage electrodes in electrical contact with a sample and a pair of current electrodes in electrical contact with the sample, wherein the voltage electrodes are disposed on the sample intermediate the current electrodes;
providing desired depths of investigation and levels of resolution by configuring the spacing of the voltage electrodes;
passing an electric current through the sample;
using a measurement device to make electrical measurements between various electrode pairs;
comparing the electrical measurements from the various electrode pairs;
inferring that the sample has heterogeneous electrical properties using the compared electrical measurements; and
adjusting, based on the electrical measurements, a finite element model (FEM) to approximate heterogeneous electrical property values.

13. The method of claim 12, wherein the sample was obtained from a subsurface formation.

14. The method of claim 12, wherein the heterogeneous electrical properties of the sample are selected from the group consisting of: resistivity, conductivity, resistance, impedance, capacitance, and inductance.

15. The method of claim 12, wherein any particular electrode pair of the various electrode pairs comprises two voltage electrodes or a voltage electrode and a current electrode.

16. The method of claim 12, further comprising detecting a resistivity anomaly within the interior of the sample.

17. The method of claim 12, wherein one particular voltage electrode is one pair member of each of the various electrode pairs.

18. A system, comprising:
a tool having two current electrodes, three or more voltage electrodes, and a measurement device capable of making electrical measurements;
a sample with electrical connectivity to one of the current electrodes at one location on the sample, the other current electrode at another location on the sample, and the three or more voltage electrodes disposed intermediate the two current electrodes; and
a processor capable of:
passing an electric current through the sample;
using the measurement device to make a first set of electrical measurements that involve a first pair of voltage electrodes;
using the measurement device to make a second set of electrical measurements that involve a second pair of voltage electrodes;
comparing the first set of electrical measurements to the second set of electrical measurements;
inferring that the sample has heterogeneous electrical properties using the compared electrical measurements; and
adjusting, based on the first set and the second set of electrical measurements, a finite element model (FEM) to approximate heterogeneous electrical property values.

19. The method of claim 18, wherein the heterogeneous electrical properties of the sample are selected from the group consisting of: resistivity, conductivity, resistance, impedance, capacitance, and inductance.

20. The method of claim 18, wherein the three or more voltage electrodes are spaced to provide various depths of investigation into the interior of the sample and high resolution measurements of the sample.

* * * * *